United States Patent [19]

Wang et al.

[11] Patent Number: 4,469,904
[45] Date of Patent: Sep. 4, 1984

[54] PREPARATION OF NITRO COMPOUNDS BY VAPOR PHASE NITRATION OF CARBOXYLIC ACIDS

[75] Inventors: Shu-Chieh P. Wang, Columbia; Martin B. Sherwin, Potomac, both of Md.

[73] Assignee: W. R. Grace & Co., New York, N.Y.

[21] Appl. No.: 510,858

[22] Filed: Jul. 5, 1983

[51] Int. Cl.³ .................... C07C 76/02; C07C 79/10
[52] U.S. Cl. .................................. 568/948; 568/927; 568/939; 568/947
[58] Field of Search ............... 568/927, 939, 947, 948

[56] References Cited

U.S. PATENT DOCUMENTS 2,894,041  7/1959  Berg ................................. 568/948
3,689,576  9/1972  Bachman et al. ................. 568/948

OTHER PUBLICATIONS

Hass et al., J. Am. Chem. Soc., vol. 76, pp. 2692 to 2694, (1954).

Primary Examiner—Leland A. Sebastian
Attorney, Agent, or Firm—Howard J. Troffkin

[57] ABSTRACT

A process for selectively forming nitro compounds by contacting, at elevated temperature and pressure and in a homogeneous gas phase, an organic carboxylic acid having from two to ten carbon atoms with $NO_2$ or $HNO_3$ alone or in the presence of oxygen and/or water.

20 Claims, 1 Drawing Figure

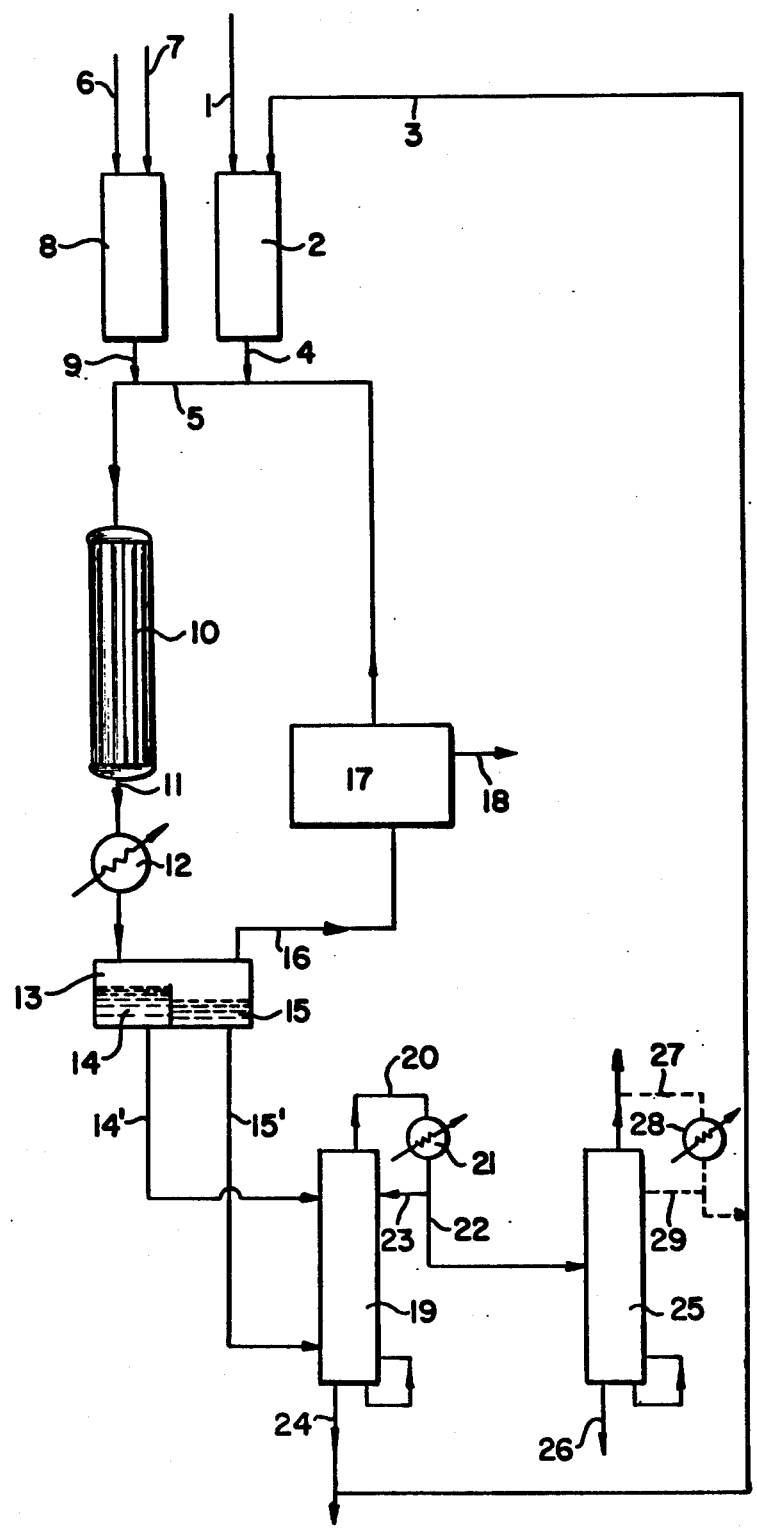

PREPARATION OF NITRO COMPOUNDS BY VAPOR PHASE NITRATION OF CARBOXYLIC ACIDS

BACKGROUND OF THE INVENTION

The present invention is directed to a process of forming a nitro compounds by gaseous phase reaction of a carboxylic acid with $NO_2$ or $HNO_3$. The present process provides a method to form pre-selected nitro-compounds based on the particular carboxylic acid feed. The process further alleviates certain processing steps required in prior art nitration of hydrocarbons.

Processes to form nitroparaffins by gaseous phase nitration are known. U.S. Pat. Nos. 3,780,115 and 3,869,253 teach that nitration of saturated hydrocarbons higher than methane can be accomplished by contacting the hydrocarbon feed with nitrogen dioxide in the presence of oxygen, such as in the form of air. The reactant gases are preheated and then introduced into the reaction zone where the gaseous phase nitration is carried out at elevated pressure and at elevated temperature. The gaseous effluent emitted from the nitration reaction zone is rapidly quenched. The quenched mixture then enters a separator where the gaseous materials are removed for subsequent purification and recycling and the remaining organic and aqueous phase liquid materials are separated by decantation and the nitroparaffins are recovered by distillation. This nitration process yields a mixture of products having a predominance of nitropropanes or nitroethanes.

French Publication No. 78/32,118 discloses that the nitroparaffins product mixture can be made to have an increased yield of nitromethane, the most commercially desired product, by utilizing ethane as the hydrocarbon feed in the homogeneous gas phase nitration. The nitration process can be further enhanced by recycling into the hydrocarbon feed some of the nitropropane product and/or by conducting the nitration in the presence of an inert gas such as nitrogen, hydrogen or argon.

U.S. Pat. No. 4,260,838, similar to the above French reference, teaches that the gas phase nitration process of U.S. Pat. Nos. 3,780,115 and 3,869,253 can be improved by altering the feed stock to obtain suitable percentages of different nitroparaffins as suits the needs of the marketplace. This patent teaches that the feed stock be made up of a mixture containing propane, preferably recycled nitroparaffin and possibly inert gas and/or another alkane. The nitrating agent can be either nitrogen dioxide or nitric acid.

Each of the conventional processes, such as those in the above referenced patents, relies on the use of a hydrocarbon feed which provides a nitroparaffin product mixture. These processes have the further defect of providing low yield of nitroparaffin mixture and low selectivity of the most commercially desired compound, nitromethane. Finally, because of the low yield, processes which are based on the gaseous phase nitration of saturated hydrocarbons produce a large volume of gaseous reaction effluents composed predominantly of unreacted hydrocarbon feed mixed with nitric oxide, carbon monoxide, carbon dioxide and inert diluent gas. The unreacted hydrocarbons must be separated and recovered from the remaining gases, such as by cryogenic means, and then recycled as part of the process feed. Such separation and recovery requires additional equipment and adds to the processing costs of the prior known processes.

A method for selectively forming particular nitroalkanes and nitroaromatics is described in U.S. Pat. No. 3,689,576. The process requires the initial formation of an acyl nitrate by the slow addition of nitric oxides or nitric acid to an acid anhydride alone or in the presence of a small amount of free acid under low temperature conditions and then thermally treating the acyl nitrate to convert it to a nitroalkane or nitroaromatic. This method has not found favor as it requires the formation and use of highly explosive acyl nitrates.

A method to selectively form particular nitroalkanes or nitroaromatics from easily available and processable feed is highly desired. It is particularly desired to have a process to selectively form nitromethane, a very industrially useful product.

SUMMARY OF THE INVENTION

An object of the present invention is to provide a process by which a selective nitro compound can be formed.

Another object of the present invention is to provide a process by which the various unreacted feed materials are readily separated and recyclable.

Another object of the present invention is to provide a process by which one can selectively form nitromethane from readily available and processable materials.

The process of the present invention is capable of selectively forming particular nitrohydrocarbon compounds by contacting in a homogeneous gas phase a $C_2$ to $C_{10}$ carboxylic acid with $NO_2$ or $HNO_3$ preferably in the presence of oxygen and/or water.

DETAILED DESCRIPTION OF INVENTION

A process for selectively forming particular aromatic or aliphatic nitro compounds comprises contacting under homogeneous gas phase reaction conditions an aromatic or aliphatic carboxylic acid with nitrogen dioxide ($NO_2$) or nitric acid preferably in the presence of oxygen.

The reactant feed of the present process can be an aliphatic or aromatic carboxylic acid. The term "carboxylic acid" as used in the present disclosure and in the appended claims refers to organic aliphatic or aromatic compounds having at least one free carboxylic acid group attached to a carbon atom of an aliphatic hydrocarbon chain, to a carbon atom of an aromatic ring or to a carbon atom of an alkaryl group.

The aliphatic carboxylic acids are selected from $C_2$ to $C_{10}$ (preferably $C_2$ to $C_5$) monocarboxylic acids or $C_3$ to $C_{10}$ (preferably $C_3$ to $C_5$) dicarboxylic acids. The preferred class of aliphatic carboxylic acid is monocarboxylic acid and of this class the compound, acetic acid, is the most preferred reactant as it selectively forms only nitromethane which is a very highly desired commercial product. In the case of monocarboxylic acids, it has been found that by selecting a monocarboxylic acid of n carbon atoms one forms the corresponding nitroalkane of n-1 carbon atoms in good yields and very high selectivity. If one uses a dicarboxylic acids of n carbon atoms one forms the corresponding nitroalkane of n-2 carbon atoms. Further, the position of the nitro group on the alkane is controlled by the selection of an acid having its carboxyl group at the carbon to be substituted. When higher aliphatic carboxylic acids are used one obtains the nitroalkane of the alkane chain of the acid as the dominant product (i.e. very high selectivity) with only small amounts of the lower nitro alkane family. For example, the nitroalkanes obtained when butyric acid is used as the feed reactant in the present process are predominantly 1-nitropropane with a very small amount of nitroethane, insignificant amount of nitromethane and no 2-nitropropane.

The present process can also form particular nitroaromatics by selectively using an aromatic carboxylic acid as the reactant feed. The carboxylic acid group can be directly bonded to a carbon atom of the aromatic ring or, alternately can be attached to the aromatic ring via an alkylene chain. The preferred aromatics are phenyl and the alkylene chain can be $C_1$-$C_{10}$ and preferably $C_1$-$C_3$.

The carboxylic acids described above preferably do not contain non-hydrocarbon groups except for the carboxyl group. However, the acids may contain non-hydrocarbon groups which will not inhibit the subject process, such as nitriles and the like.

Examples of carboxylic acids which are useful reactant feeds in the present process are acetic acid, propionic acid, butyric acid, isobutyric acid, valeric acid, isovaleric acid, caprylic acid, 6-methyl enanthoic acid, benzoic acid, phenyl acetic acid, phthalic acid, p-toluene carboxylic acid and the like. The specific acid used will, as described above, be dictated by the product desired. The most desired commercial product is nitromethane which, it has been found, can be formed in good yield and as the sole nitrocompound from acetic acid.

Nitrogen dioxide (the terms "nitrogen peroxide" and "nitrogen dioxide" as used in this disclosure and in the claims appended hereto each refer to the compound $NO_2$) or its precursers, $N_2O_4$ or nitric acid (which dissociates to $NO_2$ and water under the reaction conditions described below), are readily obtainable materials.

It is preferred that the feed also includes oxygen, usually in the form of air. The oxygen as well as the nitrogen dioxide can be at least partially obtained from recycled unreacted materials which have been separated and purified by conventional method from the reaction product as more fully described below.

The feed may further contain inert gas such as nitrogen, carbon monoxide, carbon dioxide, argon or mixtures thereof. Further, the feed can contain water either as a carrier for the carboxylic acid reactant feed or as a part of the nitrating agent.

The conditions and parameter ranges for conducting the homogeneous gaseous nitration of a carboxylic acid are (a) that the reaction zone contains a molar ratio of carboxylic acid to $NO_2$ or $HNO_3$ of from about 0.3 to 3 or greater and preferably from 0.5 to 3. The environment can be, therefore, either a reducing or an oxidizing environment depending on the feed ratio used. When oxygen is used as an additional feed, it should be present in from about 0.05 to 1 mole and preferably 0.1 to 0.5 mole per mole of $NO_2$ or $HNO_3$. The reaction is carried out at elevated temperature of from about 200° C. to about 500° C.and preferably from about 250° C. to 400° C. The reaction is carried out under elevated pressure of from about 1 to ° bars with from 2 to 12 bars being preferred. The combined temperature and pressure conditions must be such as to maintain the reactants in a homogeneous gas phase. The inert gases in the feed (A, CO, $CO_2$, $N_2$) can be from about 0 to 90 volume percent. The water can be from about 0 to 30 weight percent based on the $NO_2$ with at most 10 being preferred. The reaction contact time of the reaction gases in the reaction zone can be from about 1 to 20 seconds with the order of from about 4 to 12 seconds being preferred.

Referring to the drawing to illustrate the subject process, a carboxylic acid such as acetic acid, propionic acid, etc. is transported from a reservoir (not shown) by pipeline 1 to preheater 2. Preheater 2 is also used to preheat the aqueous carboxylic acid being recirculated through pipeline 3, as more fully described hereinbelow. The preheater is maintained at substantially the reaction zone entry temperature of about 200° C. to 500° C. and pressure of from about 1 to 20 bars. The preheated carboxylic acid is then passed through pipeline 4 to reactor intake pipeline 5. The nitrogen dioxide and the oxygen (when used) are introduced to preheater 8 via pipelines 6 and 7, respectively. The preheater 8 is maintained at temperature and pressure conditions substantially the same as that of preheater 2. The mixed preheated $NO_2/O_2$ gases pass through pipeline 9 to reactor intake pipeline 5 using gas-gas mixing devices such as spargers, venturis, etc. The preheated gases are passed through reactor 10 which may be in the form of a tubular reactor capable of maintaining a reaction temperature of from about 200° C. to 500° C., preferably from about 250° C. to 400° C. and a pressure of approximately 1 to 20, preferably about 2 to 12 bars. The reactor effluents withdrawn through pipeline 11 are cooled to ambient temperature in cooler 12 which uses supercooled water to rapidly cool the gases. The cooled reactor effluents are separated in the separator 13. The liquid effluent separates into organic liquid phase 14 and aqueous liquid phase 15.

The uncondensed gaseous reaction effluents are removed from the separator 13 through pipeline 16. The uncondensed gaseous reaction effluents which are obtained in the present process are generally a mixture of components composed predominantly of nitrogen monoxide and inert gases. These effluent gases are distinctly different from those encountered in conventional hydrocarbon gaseous nitration processes where the effluent gases are rich in the unreacted hydrocarbons which must be separated from the nitrogen monoxide (which must be separately treated) and recycled as part of the feed. Such separation is complex and costly. In contrast, the uncondensed effluent gases of separator 13 is substantially free of unreacted carboxylic acid and thereby do not require separation. Instead, in the present process the effluent gases of separator 13 can be directly and readily treated at station 17 to re-oxidize the nitrogen oxide to nitrogen dioxide for reuse by, for example, directly injecting oxygen into the gaseous effluent. To prevent build-up of inert gases due to the recycling of gaseous effluent, a purge stream 18 is maintained.

The condensed organic and aqueous liquid phases 14 and 15, respectively, are removed from separator 13 and sent by pipelines 14' and 15' to an azeotropic distillation column 19. When the nitro compound product has a lower density than water (i.e. some $C_4$ and higher nitro compounds) the organic and aqueous liquid phases 14 and 15 will be in reversed position in separator 13 to that shown. In such instances (not shown) line 14' will enter the bottom portion of column 19 and line 15' will enter the top portion of column 19. Azeotropic distillation column 19 normally operates at a pressure of about 1.25 bars or less and at temperatures sufficient to remove overhead the nitroalkane or nitroaromatic products as well as other by-product compounds having a boiling point lower than the nitro product with their associative water. These materials are passed via pipeline 20, condenser 21 and pipeline 22 to a by-product removal distillation column 25. Some of the distillate may be recycled to column 19 by pipeline 23. The majority of the water and the majority of unreacted carboxylic acid are readily removed as bottom products through pipeline 24 and recycled directly to intake pipe 3 to preheater 2 or are removed through pipeline 24 and treated (not shown) to remove some of all of the water such as by distillation, and then recycled to intake pipe 3 to preheater 2.

The by-product removal column 25 operates at a pressure of 1.25 bars or less and at a temperature of from about 30° C. to 95° C. which is sufficient to remove any by-products, such as lower oxygenated hydrocarbons, from the nitro products. The bottom product of column 25 is removed by pipeline 26 and is composed of the nitroalkane or mixture of nitroalkanes or nitroaromatic, as is appropriate based on the carboxylic acid feed. In addition, there may be present a small amount of water (from the prior azeotropic distillation) and traces of by-product. The material removed by pipeline 26 is subsequently chemically treated (not shown) to remove the trace contaminants then fed to a dehydration column (not shown) and finally, if necessary, to a fractionation column (not shown) to recover pure nitroparaffin products.

The overhead effluent of column 25 is removed by pipeline 27. The overhead effluent is normally very small in comparison to the bottom product and is made up of a mixture of materials. Due to its small quantity, its mixed composition and the difficulty of purification into individual components, the effluent of pipeline 27 is normally incinerated. However, when a higher carboxylic acid is utilized as feed the effluent of pipeline 27 may contain a mixture of lower alcohols, aldehydes, lower acids and the like which can be recycled by pipeline 28 to pipeline 24 along with the carboxylic acid. These oxygenated hydrocarbons have been found to promote the formation of nitroalkanes.

It has been unexpectedly found that by utilizing a free carboxylic acid compound as described above one can provide a process which can be directed to form a particular nitro compound or at least to form a particular nitro compound in very high selectivity not attainable by the present commercial mode of forming nitroparaffins by homogeneous nitration of alkanes. Further, such commercial processes do not produce high degrees of nitration of the feed on any one pass through the reactor. It is, therefore, necessary to provide a means to readily recover and recycle the starting feed. In present commercial processes using alkane feeds, this separation and recycling is both difficult and costly. The presently utilized carboxylic acid which are readily separated and easily returned as reactor feed.

The following examples are given for illustrative purposes only and are not meant to be a limitation on the invention as defined by the claims appended hereto. All parts and percentages are by weight unless otherwise indicated.

EXAMPLE I

A production run was performed using acetic acid as the carboxylic acid feed. Each feed material was preheated to 300° C. at 10 bars. The materials were then mixed and reacted in a tubular reactor at operating pressure of 10 bars, a jacket temperature of 300° C. and a contact time of 8 seconds. The individual feed rates (all rates are in mmoles/hour) of 1115 for acetic acid, 629 for $NO_2$, 447 for oxygen and 6515 for nitrogen. The reaction produced, on a one pass basis, 68 mmoles/hour of nitromethane, 51 mmoles/hour of carbon monoxide, 287 mmoles/hour of carbon dioxide and 55 mmoles/hour of other $C_1$ compounds. The yield of nitromethane was 17 percent based on the total carbon compounds obtained. No other nitro compound was obtained.

EXAMPLE II

A series of production runs were performed under the same reactor conditions as described in Example I above. All of the runs were performed under an oxidizing environment as determined by the acetic acid/nitrogen dioxide ratio. The runs were run with and without addition of water and with and without oxygen. Table I below gives the reactant feed rates and nitromethane molar yield (defined molar ratio of nitromethane produced divided by acetic acid consumed times one hundred to give yield in percentage).

TABLE I

| Run No. | 1 | 2 | 3 |
|---|---|---|---|
| Temperature (°C.) | 300 | 300 | 300 |
| Pressure (atm) | 10 | 10 | 10 |
| Feed | | | |
| Acetic Acid | 410 | 487 | 1107 |
| Nitrogen Dioxide | 1386 | 1441 | 1513 |
| Water | 326 | 387 | 0 |
| Oxygen | 492 | 0 | 0 |
| Nitrogen | 7293 | 7810 | 7810 |
| % Acetic Acid Conversion to $C_1$ Compounds per Pass | 41.4 | 38.9 | 43.5 |
| Nitromethane Molar Yield | 37 | 37 | 44 |

The above data shows that nitromethane is produced in good yields, that the presence of oxygen and/or water do not effect the nitromethane production when done under oxidizing conditions. The higher acetic acid/nitrogen dioxide ratio when increased from 0.3 to 0.7 tends to favor nitromethane production.

EXAMPLE III

A series of production runs were conducted using the same reaction conditions as described in Example I above except that the reactor temperature was varied. The ratio of acetic acid to nitrogen dioxide was varied from 1.8 to 3.3 and thereby provided a reducing environment. Detailed operating conditions and nitromethane molar yield are summarized in Table II below:

TABLE II

| Run No. | 1 | 2 | 3 | 4 |
|---|---|---|---|---|
| Temperature (°C.) | 300 | 250 | 280 | 280 |
| Pressure (atm) | 10 | 10.2 | 10 | 10 |
| Feed mmoles/hr | | | | |
| Acetic Acid | 2897 | 3056 | 2925 | 3088 |
| Nitrogen Dioxide | 1610 | 1588 | 879 | 958 |
| Nitrogen | 7918 | 1737 | 4018 | 3689 |
| Oxygen | 0 | 0 | 0 | 314.2 |
| % Acetic Acid Conversion to $C_1$ Compounds per Pass | 23.6 | 10.8 | 13.8 | 14.1 |
| Nitromethane Molar Yield | 51 | 44 | 49.8 | 41.8 |

Gas chromatograph/Mass spectroscopy analysis of the product stream showed no additional nitro product besides nitromethane.

EXAMPLE IV

A series of production runs were performed using propionic and butyric acids. The feed rates, the conversion on a per pass basis and the carbon selectivity are given in Table III below:

TABLE III

| Run No. | 1 | 2 | 3 |
| --- | --- | --- | --- |
| Reactor Conditions | | | |
| Temperature (°C.) | 250 | 300 | 300 |
| Pressure (atm) | 10 | 10 | 10 |
| Residence Time (sec) | 8.7 | 8 | 8.1 |
| Feed mmoles/hr | | | |
| Propionic Acid | 937 | 910 | 0 |
| Butyric Acid | 0 | 0 | 692 |
| Nitrogen Dioxide | 839 | 796 | 874 |
| Nitrogen | 7918 | 7918 | 7918 |
| Acid Conversion (%) | 9.5 | 30.7 | 42 |
| Carbon Selectivity (%) | | | |
| Nitromethane | 2.4 | 3.3 | 1.0 |
| Nitroethane | 24.9 | 24.4 | 6.0 |
| 1-nitropropane | 0 | 0 | 23.4 |
| 2-nitropropane | 0 | 0 | 0 |
| $CO_x$ | 52.7 | 56 | 38.4 |
| Lower Oxygenates | 9.7 | 4.9 | 24.7 |

The above runs show that by selecting a particular n carbon atom carboxylic acid one obtains the (n-1) carbon nitroalkane in very high selectivity. Further, the position of the nitro group is specifically controlled by the position of the carboxyl group.

EXAMPLE V

A production run was conducted under the same conditions as described in Example I above except that a molar equivalent of phenylacetic acid was used instead of acetic acid. Alpha-nitrotoluene was formed in 36% yields as determined by GPC anlysis of the products formed.

While the invention has been described in connection with certain preferred embodiments, it is not intended to limit the invention to the particular form set forth, but, on the contrary, it is intended to cover such alternatives, modifications and equivalents as defined by the appended claims.

What is claimed is:

1. A process for selectively forming nitroalkanes and nitroaromatics comprising contacting in a reaction zone at an elevated pressure of from about 1 to about 20 bars and temperature of from about 200° C. to about 500° C. to provide a homogeneous gas phase, a carboxylic acid selected from $C_2$–$C_{10}$ aliphatic monocarboxylic acids, $C_3$–$C_{10}$ aliphatic dicarboxylic acids, aromatic carboxylic acids, and mixtures thereof, with nitrogen dioxide or nitric acid or both and recovering the formed nitro compound.

2. The process of claim 1 wherein the reaction zone further contains oxygen, water or both.

3. The process of claim 1 wherein the carboxylic acid is at least one $C_2$–$C_5$ aliphatic monocarboxylic acid.

4. The process of claim 2 wherein the carboxylic acid is at least one $C_2$–$C_5$ aliphatic monocarboxylic acid.

5. The process of claim 1 wherein the carboxylic acid is an aromatic carboxylic acid.

6. The process of claim 2 wherein the carboxylic acid is an aromatic carboxylic acid.

7. The process of claim 1 wherein the carboxylic acid is selected from the group consisting of acetic, propionic and butyric acid.

8. The process of claim 2 wherein the carboxylic acid is selected from the group consisting of acetic, propionic and butyric acid.

9. The process of claim 2 wherein the reaction zone has a pressure of from about 2 to 12 bars, a temperature of from about 250° C. to 400° C., the molar ratio of $O_2$ to $NO_2$ or $HNO_3$ feed of from about 0.05 to 1 mole and the molar ratio of carboxylic acid to $NO_2$ or $HNO_3$ feed of from about 0.3 to about 3.

10. The process of claim 4 wherein the reaction zone has a pressure of from about 2 to 12 bars, a temperature of from about 250° C. to 400° C., the molar ratio of $O_2$ to $NO_2$ or $HNO_3$ feed of from about 0.05 to 1 mole and the molar ratio of carboxylic acid to $NO_2$ or $HNO_3$ feed is from about 0.3 to about 3.

11. The process of claim 1 further comprising cooling the reaction zone effluent, separating the resulting liquid phase effluent from the non-condensed gaseous effluent, separating any unreacted carboxylic acid and returning at least a portion of said unreacted acid to the reaction zone.

12. The process of claim 2 further comprising cooling the reaction zone effluent, separating the resulting liquid phase effluent from the non-condensed gaseous effluent, separating any unreacted carboxylic acid and returning at least a portion of said unreacted acid to the reaction zone.

13. The process of claim 3 further comprising cooling the reaction zone effluent, separating the resulting liquid phase effluent from the non-condensed gaseous effluent, separating any unreacted carboxylic acid and returning at least a portion of said unreacted acid to the reaction zone.

14. The process of claim 4 further comprising cooling the reaction zone effluent, separating the resulting liquid phase effluent from the non-condensed gaseous effluent, separating any unreacted carboxylic acid and returning at least a portion of said unreacted acid to the reaction zone.

15. The process of claim 5 further comprising cooling the reaction zone effluent, separating the resulting liquid phase effluent from the non-condensed gaseous effluent, separating any unreacted carboxylic acid and returning at least a portion of said unreacted acid to the reaction zone.

16. The process of claim 6 further comprising cooling the reaction zone effluent, separating the resulting liquid phase effluent from the non-condensed gaseous effluent, separating any unreacted carboxylic acid and returning at least a portion of said unreacted acid to the reaction zone.

17. The process of claim 7 further comprising cooling the reaction zone effluent, separating the resulting liquid phase effluent from the non-condensed gaseous effluent, separating any unreacted carboxylic acid and returning at least a portion of said unreacted acid to the reaction zone.

18. The process of claim 8 further comprising cooling the reaction zone effluent, separating the resulting liquid phase effluent from the non-condensed gaseous effluent, separating any unreacted carboxylic acid and returning at least a portion of said unreacted acid to the reaction zone.

19. The process of claim 9 further comprising cooling the reaction zone effluent, separating the resulting liquid phase effluent from the non-condensed gaseous effluent, separating any unreacted carboxylic acid and returning at least a portion of said unreacted acid to the reaction zone.

20. The process of claim 10 further comprising cooling the reaction zone effluent, separating the resulting liquid phase effluent from the non-condensed gaseous effluent, separating any unreacted carboxylic acid and returning at least a portion of said unreacted acid to the reaction zone.

* * * * *